US009690989B2

(12) United States Patent
Hay (10) Patent No.: US 9,690,989 B2
(45) Date of Patent: Jun. 27, 2017

(54) FOSSIL RECOGNITION APPARATUS, SYSTEMS, AND METHODS

(75) Inventor: Richard Thomas Hay, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/370,925

(22) PCT Filed: Jan. 19, 2012

(86) PCT No.: PCT/US2012/021861
§ 371 (c)(1),
(2), (4) Date: Jul. 7, 2014

(87) PCT Pub. No.: WO2013/109277
PCT Pub. Date: Jul. 25, 2013

(65) Prior Publication Data
US 2014/0377873 A1    Dec. 25, 2014

(51) Int. Cl.
*G06K 9/00* (2006.01)
*G01N 33/24* (2006.01)
(Continued)

(52) U.S. Cl.
CPC ............ *G06K 9/0063* (2013.01); *E21B 47/00* (2013.01); *E21B 47/0002* (2013.01);
(Continued)

(58) Field of Classification Search
CPC ...... G06K 9/00; G06K 9/00221; G01N 33/24; G01N 33/241; E21B 47/00
(Continued)

(56) References Cited

U.S. PATENT DOCUMENTS 2,297,083 A * 9/1942 Svensson ...................... 530/203
5,109,697 A * 5/1992 Millheim et al. .......... 73/152.11
(Continued)

FOREIGN PATENT DOCUMENTS

CN    1912341 A    2/2007
EP    0747569 A2    12/1996
(Continued)

OTHER PUBLICATIONS

"International Application Serial No. PCT/US2012/021861, International Preliminary Report on Patentability mailed Apr. 17, 2014", 4 pgs.
(Continued)

*Primary Examiner* — Krishnan S Menon
*Assistant Examiner* — Dwan A Gerido
(74) *Attorney, Agent, or Firm* — Gilliam IP PLLC (57) ABSTRACT

In some embodiments, an apparatus and a system, as well as a method and an article, may operate to acquire fluid image information from an imaging device having a field of view including fluid, the fluid image information including fossil image information. Additional activities may include processing the fossil image information to identify fossil types in the fluid as data that associates the fossil types with a formation from which the fluid was acquired, determining the location of a first borehole in the formation based on the data and offset records associated with a second borehole, and publishing the data in conjunction with indications of the location. Additional apparatus, systems, and methods are disclosed.

20 Claims, 8 Drawing Sheets

(51) Int. Cl.
E21B 47/00 (2012.01)
E21B 47/12 (2012.01)
E21B 49/08 (2006.01)

(52) U.S. Cl.
CPC .............. *E21B 47/12* (2013.01); *E21B 49/08* (2013.01); *E21B 49/081* (2013.01); *G01N 33/241* (2013.01); *G06K 9/00221* (2013.01)

(58) Field of Classification Search
USPC .......................................................... 436/29
See application file for complete search history.

(56) References Cited

U.S. PATENT DOCUMENTS

| | | | |
|---|---|---|---|
| 7,458,252 | B2 | 12/2008 | Freemark et al. |
| 2006/0243033 | A1 | 11/2006 | Freemark et al. |
| 2008/0235032 | A1* | 9/2008 | Emam et al. ................. 704/275 |
| 2009/0080705 | A1* | 3/2009 | Orpen .................... G01N 33/24 382/109 |
| 2010/0015601 | A1* | 1/2010 | Gilmore et al. .................. 435/6 |
| 2010/0245096 | A1 | 9/2010 | Jones et al. |
| 2010/0258304 | A1* | 10/2010 | Hegeman ................. 166/250.01 |
| 2010/0332210 | A1* | 12/2010 | Birdwell et al. ................ 703/22 |

FOREIGN PATENT DOCUMENTS

| | | | |
|---|---|---|---|
| EP | 1882809 | A1 | 1/2008 |
| EP | 2028341 | A1 | 2/2009 |

OTHER PUBLICATIONS

"International Application Serial No. PCT/US2012/021861, Search Report mailed May 4, 2012", 2 pgs.
"International Application Serial No. PCT/US2012/021861, Written Opinion mailed May 4, 2012", 6 pgs.
Breard, S. Q., et al., "Paleoecologic and Biostraigraphic Models for Pleistocene Through Miocene Foraminiferal Assemblages of the Gulf Coast Basin", Transactions, Gulf Coast Association of Geological Societiies, 43, (1993), 493-502.
Davies, E. H., et al., "Petroleum Exploration Application of Palynological Assemblage Successions in the Flexure Trend, Gulf of Mexico", In: Innovative Biostratigraphic Approaches to Sequence Analysis: New Exploration Opportunities, (Eighth Annual Research Conference—Guf Coast Section, Society of Economic Paleontologists and Mineralogists Foundation, Houston, TX, Dec. 6-9, 1987), (1987), 47-51.
Tipsword, H. L., et al., "Interpretation of Depositional Environment in Gulf Coast Petroleum Exploration From Paleoecology and Related Stratigraphy", Transactions, Gulf Coast Association of Geological Societiies, 16, (Sixteenth Annual Convention of G.C.A. G.S. and the 1966 Fall Regional Meeting of the American Association of Petroleum Geologists, Oct. 36-29, 1966, Lafayette, LA), (1966), 119-130.
Ventress, W. P. S., "Paleontology and its application in South Louisiana Hydrocarbon Exploration", In: An Introduction to Central Gulf Coast Geology, D. Goldthwaite, Editor, (1991), 85-97.
"European Application Serial No. 12866255.8, Response filed Feb. 11, 2015 to Office Action mailed Dec. 10, 2014", 2 pgs.
"International Application Serial No. PCT/US2012/021861, Response filed Jul. 25, 2012 to Written Opinion mailed May 4, 2012", 4 pgs.
Fleisher, Robert L., et al., "Chapter 17—Applied Paleontology", In: *Exploring for Oil and Gas Traps, Handbook No. 3, Treatise of Petroleum Geology*, Beaumont, Edward A., et al., Editors, (2000), 17-1-17-65.

"European Application Serial No. 12866255.8, Supplementary European Search Report mailed Mar. 5, 2015", 6 pgs.
"Canadian Application Serial No. 2,861,305, Office Action mailed Sep. 23, 2014", 6 pgs.
"European Application Serial No. 12866255.8, Office Action mailed Dec. 10, 2014", 2 pgs.
"Imagu Object Recognition Software", [online]. © 2009 Imagu Ltd. [archived on Dec. 25, 2010]. Retrieved from the Internet: <URL: https://web.archive.org/web/20101225002513/http://www.imagutech.com/technology.html>, (2009), 2 pgs.
Abu-Zied, Ramadan, "Introductory Micropaleontology", [online]. [archived Aug. 30, 2007]. Retrieved from the Internet: <URL: https://web.archive.org/web/20070830092249/http://osp.mans.edu.eg/abuzied/Micropaleontology.htm>, (2007), 2 pgs.
Dollar, P., et al., "Multiple Component Learning for Object Detection". Computer Vision—ECCV 2008, Lecture Notes in Computer Science, vol. 5303, (2008), 211-224.
Jones, Robert W., et al., "Chapter 15—The Role and Value of "Biosteering" in Hydrocarbon Reservoir Exploitation", Springer Link, *Applied Statigraphy—Topics in Geobiology*, vol. 23, (2005), 339-355.
Tu, Zhuowen, et al., "Image Parsing: Unifying Segmentation, Detection, and Recognition", *International Journal of Computer Vision*, 63(2), (2005), 113-140.
Whymark, Aubrey, "Basic Guide to Geosteering", www.geosteering.co.uk, [online]. [retrieved on Sep. 22, 2014]. Retrieved from the Internet: <https://onedrive.live.com/view.aspx?resid=D5084C9816B9FB43!106&app=WordPdf&wdo=2&authkey=!AAm8caWPIP07S2I, (Dec. 2010), 12 pgs.
"Canadian Application Serial No. 2,861,305, Response filed Mar. 18, 2015 to Office Action mailed Sep. 23, 2014", 23 pgs.
"Canadian Application Serial No. 2,861,305, Response filed Oct. 13, 2015 to Office Action mailed Apr. 14, 2015", 34 pgs.
"European Application Serial No. 12866255.8, Office Action mailed Dec. 17, 2015", 4 pgs.
"Russian Application Serial No. 2014130990, Office Action mailed Dec. 10, 2015", (w/ English Translation), 6 pgs.
"Canadian Application Serial No. 2,861,305, Office Action mailed Nov. 18, 2015", 4 pgs.
"Canadian Application Serial No. 2,861,305, Response filed Feb. 5, 2016 to Office Action mailed Nov. 18, 2015", 17 pgs.
"Russian Application Serial No. 2014130990, Response filed Feb. 3, 2016 to Office Action mailed Dec. 10, 2015", (w/ English Translation of the Claims), 10 pgs.
"Australian Application Serial No. 2012366288, First Examiner Report mailed Aug. 24, 2015", 4 pgs.
"Canadian Application Serial No. 2,861,305, Office Action mailed Apr. 14, 2015", 11 pgs.
"European Application Serial No. 12866255.8, Response filed Sep. 9, 2015 to Extended European Search Report mailed Mar. 5, 2015", 17 pgs.
"European Application Serial No. 12866255.8, Response filed Sep. 12, 2016 to Communication Pursuant to Article 94(3) EPC mailed Jul. 5, 2016", 10 pgs.
"Canadian Application Serial No. 2,861,305, Office Action mailed Feb. 23, 2016", 5 pgs.
"Chinese Application Serial No. 201280067536.4, Office Action mailed Mar. 30, 2016", W/ English Translation, 27 pgs.
"European Application Serial No. 12866255.8, Response filed Feb. 29, 2016 to Communication Pursuant to Article 94(3) EPC mailed Dec. 17, 2015", 11 pgs.
"Australian Application Serial No. 2012366288, Response filed Mar. 24, 2016 to First Examiner Report mailed Aug. 24, 2015", 20 pgs.
"Canadian Application Serial No. 2,861,305, Response filed May 24, 2016 to Office Action mailed Feb. 23, 2016", 13 pgs.
"European Application Serial No. 12866255.8, Communication Pursuant to Article 94(3) EPC mailed Jul. 5, 2016", 3 pgs.

* cited by examiner

FOSSIL RECOGNITION APPARATUS, SYSTEMS, AND METHODS

PRIORITY APPLICATION

This application is a U.S. National Stage Filing under 35 U.S.C. 371 from International Application No. PCT/US2012/021861, filed on 19 Jan. 2012, and published as WO 2013/109277 on 25 Jul. 2013; which application and publication is incorporated herein by reference in its entirety.

BACKGROUND

Microfossils are the fossil remains of unicellular and multicellular micro-organisms and the dissociated elements and skeletal fragments of macro-organisms. They include the fossil types Foraminifera, Ostracods, Coccolithophora, Diatoms, Radiolaria and Dinoflagellates, among others. These fossils can be found in many levels of a geological formation.

Biostratigraphy can be useful in building geologic models for hydrocarbon exploration and in the drilling operations that test those models. By understanding the structure and properties of geological formations, the cost of drilling wells for oil and gas exploration can be reduced. For this reason fossils, including micofossils, are manually examined as they appear in cuttings brought up from down hole drilling and cleaning operations. However, these current examination methods are prone to human error, and it is sometimes difficult to determine the origin of the cuttings/fossils, especially in vertical exploration wells.

DETAILED DESCRIPTION

Microfossils and nanofossils behave as formation markers that are currently interpreted by a human. For the purposes of this document, a microfossil measures about 1-1000 micrometers in diameter, and a nanofossil measures about 1-1000 nanometers in diameter. Hereinafter, the term "fossil" will be used to mean both microfossils and nanofossils. Thus, fossils are currently examined on the surface by paleontologists, using a microscope to view cuttings brought up to the surface from down hole.

To address some of the challenges described above, as well as others, apparatus, systems, and methods to automatically identify fossils in formation fluid samples taken at known depths are described. This mechanism aids in the accurate determination of formation characteristics and structure, perhaps obviating the need to employ a paleontologist. Images can be transmitted to the surface via high speed telemetry, and sent to an expert to be examined should confirmation of the finding by the fossil identification mechanism located down hole be desired. The image could also be processed on the surface with more powerful computing systems to identify fossils in the images sent to the surface. In addition, the information developed may sometimes be used to adjust drilling operations via biosteering in real-time.

Some embodiments combine their fossil identification output (i.e., the identification of fossil types) with the output of a down hole fluid identification system. In this way, the fossils in a particular fluid sample can be identified to obtain specific information about the formation characteristics from the fluid is being taken.

Figure 1:
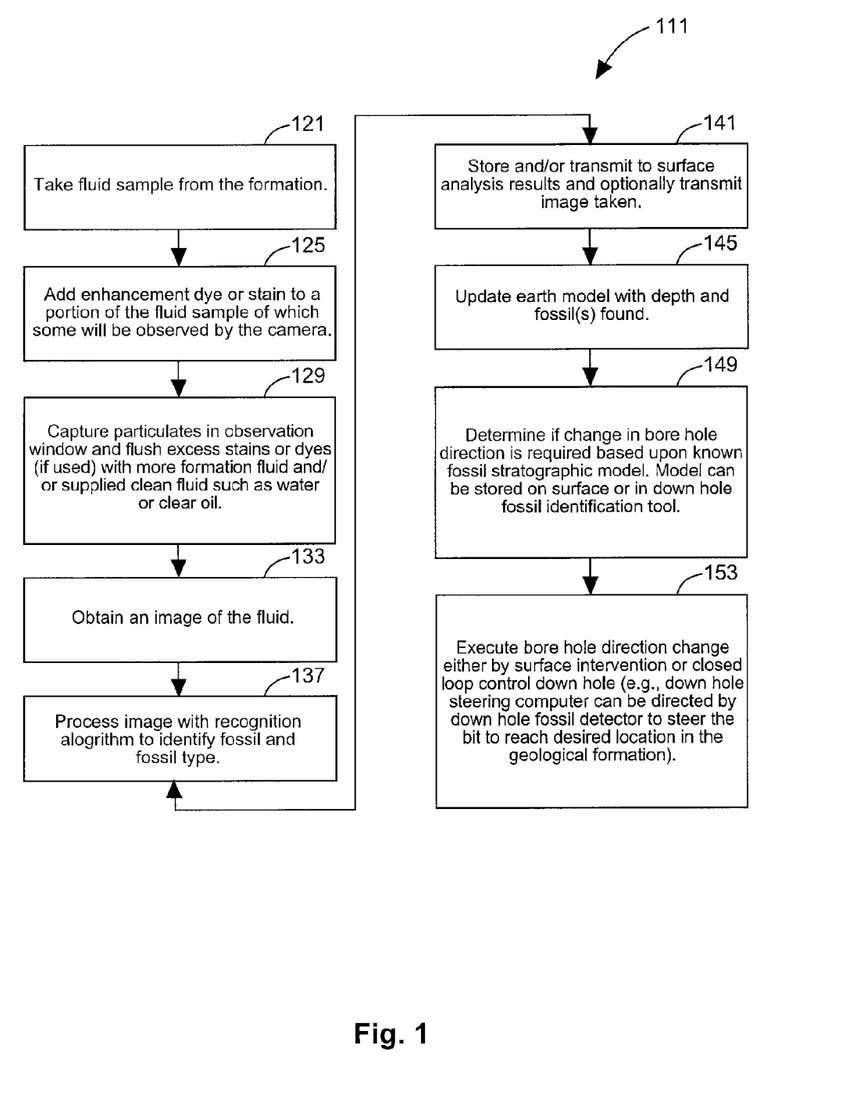
FIG. 1 is a flow chart illustrating several methods according to various embodiments of the invention.

FIG. 1 is a flow chart illustrating several methods 111 according to various embodiments of the invention. In some embodiments, the methods 111 begin at block 121 with drawing formation fluid into a sampling tool, either using a wire line, or as part of a logging while drilling (LWD) string.

At block 125, to enhance the identification of fossils, a dye can be mixed with the fluid sample. The dye might be formulated to adhere to or react with calcium carbonate and/or other components typically found in fossils. The dye enhancement may be used to assist an algorithm that searches fossil image information for a particular color, to better define the extents of a particular fossil particle to be identified in the image.

The observation window in a fluid receptacle can be flushed at block 129 between samples with a clean fluid like water or clear oil stored inside a down hole tool, or simply left as-is and flushed with the next sample of fluid or mud.

In block 133, the fluid passes through a thin observation receptacle formed by two optically transparent windows. A light and microscope fitted with a digital camera can be used to record an image of particles suspended in the fluid as fluid image information, while the sample flows past the sample window. Sampling can be halted to allow the camera to take still images at desired intervals, or if the camera is able to gather images quickly, continuous flow can occur.

To search for various sizes of fossils in the fluid, the microscope can change its magnification to ensure large and small fossils can be observed by adjusting the zoom of the lens, switching the lens, or using another camera with a different zoom value. The microscope can also be directed by the processor to zoom in on particles both optically and/or digitally to obtain a better definition of the shape of the fossil, improving identification. Multiple microscopes or changeable lenses can be used to vary the zoom level. Multiple sample plates, including plates with colored windows, can also be used with multiple microscopes, in any combination. Spectral cameras, such as the Arrow™ hyperspectral imaging video camera available from Rebellion Photonics LLC of Houston, Tex. can be used to look for calcium carbonate in the fluid to help identify where fossils are likely to be found in the image.

Images can be provided in video or still frame format. The fluid image information is sent to a processor which executes a recognition program that processes the fluid image information at block 137 to search and recognize objects in the image, usually in digital form, as various fossil types.

The algorithm used for fossil recognition can be adapted from those used for fingerprint identification, or face recognition, among others. These include algorithms similar to or identical to those provided by the PAX-it image management and analysis software available from MIS Inc. of Villa Park, Ill. and the Split-Online® automated digital image analysis system available from Split Engineering LLC, as well as the SureMatch 3D facial recognition software suite available from Genex Technologies, Inc. of Bethesda, Md. Other software and processing instructions may be used, based on technical needs and flexibility desired.

A memory located down hole may be used to store representations of what the recognition algorithm should use to search during image matching. For example, the image forms of various types of microfossils, including benthic, planktonic foraminifera, calcareous nannofossils, palynomorphs, and other particles that can be optically identified can be used to indicate the formation layer from which a particular fluid sample has been extracted.

At block 141, the result is stored as fossil image information in a memory and/or transmitted as identifications made of determined fossil types observed in the fluid. Fluid containing certain fossils can be automatically stored if the fossil recognition tool finds a desired fossil type or a cluster of combined fossils within the fluid.

The processor can also be trained to ignore particulates, such as sand grains, that are not of interest. Dyes can be added to demarcate sand, shale, and mud particles like barite, to be more easily excluded from fossil detector processing. The detector can also be used to record the type and size of various non-fossil particulates observed, storing the results in memory as desired. The density and size of observed particulates can also be an indicator of the formation competency and can be recorded and stored in memory, and/or transmitted to the surface in real-time.

At block 145, existing Earth models can be updated with the depth, concentration, and identification of fossil types that have been identified.

At block 149, the first part of a biosteering process can be implemented. That is, based on the known fossil stratigraphic record, the presence or absence of selected fossil types can be used to determine whether a change in drill bit direction should be made.

At block 153, the second part of biosteering can be implemented. Here the change in direction is made via human intervention, or via closed loop control, to command the drill bit to continue on course, or to go in a different direction, so as to reach a desired location in the geological formation. Such geological information coupled with the biostrata model can be located in local memory in the down hole fossil computer. The steering computer can calculate and then execute an optimal path, based on limitations of the steering assembly and possibly offset data from other wells to optimize a new path to the change in position of the desired target based on the results from the fossil analysis. Additional embodiments may be realized.

Figure 2A:
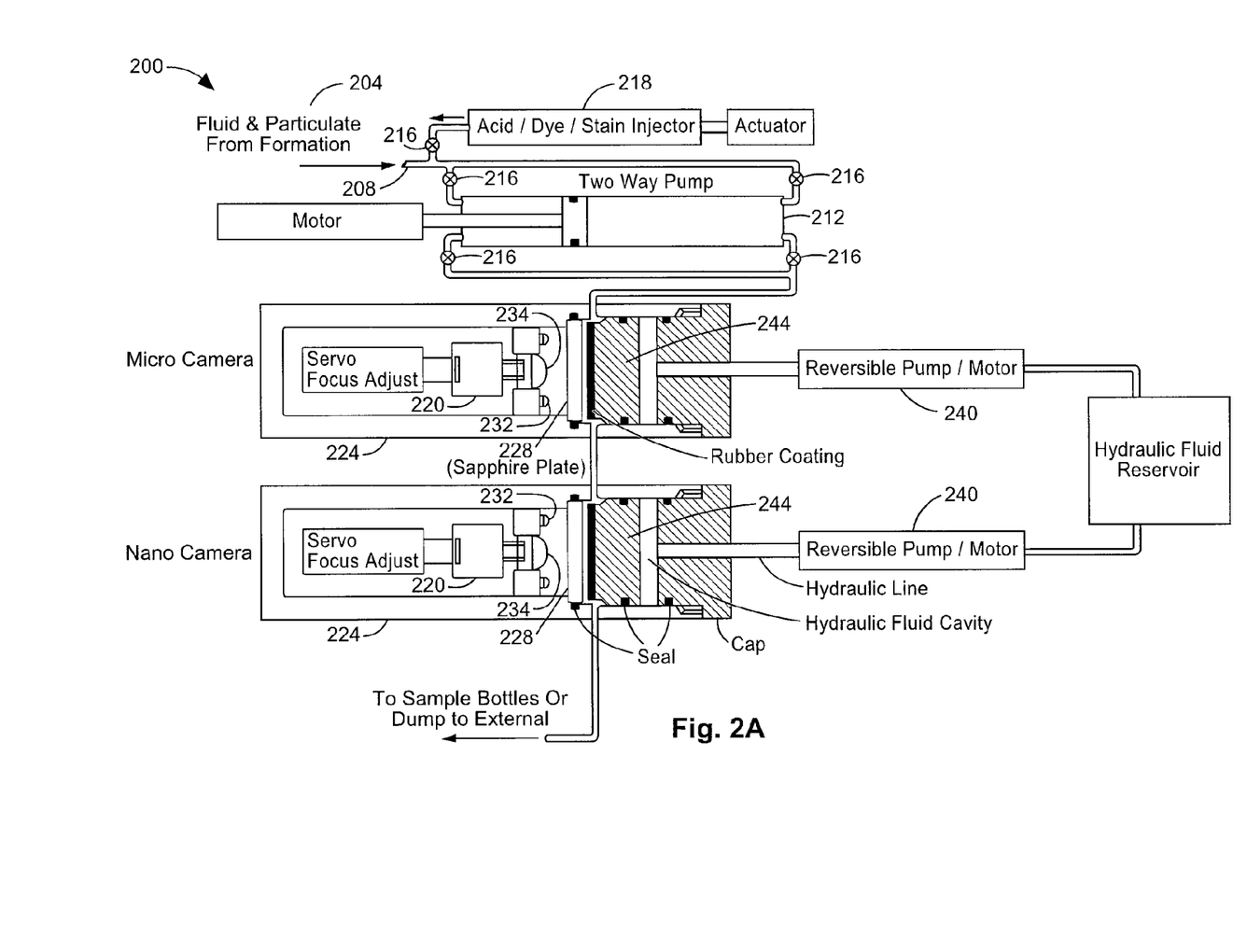
FIGS. 2A and 2B are block diagrams of apparatus and systems according to various embodiments of the invention.
Figure 2B:
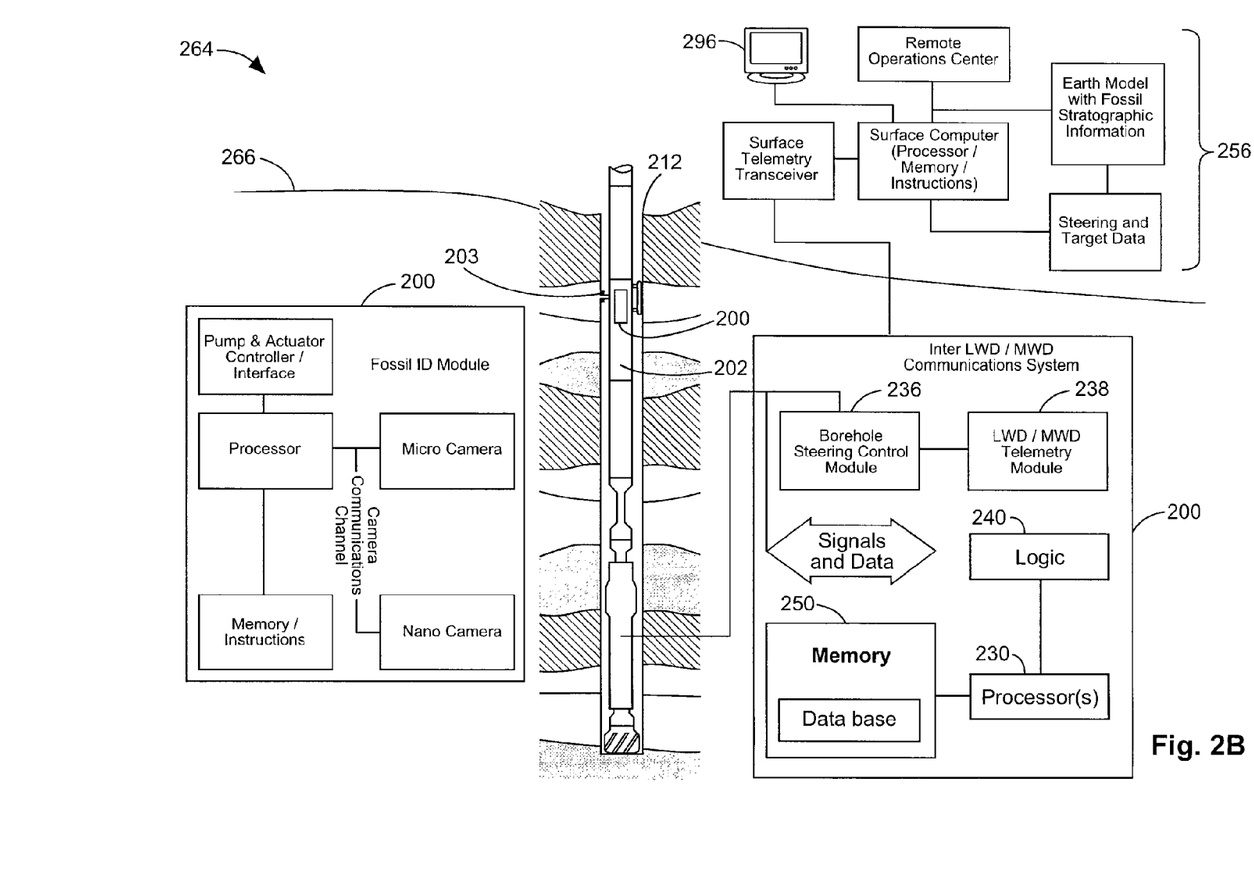

For example, FIGS. 2A and 2B are block diagrams of apparatus 200 and systems 264 according to various embodiments of the invention. Turning now to FIG. 2A, it can be seen that formation fluid 204 from the formation sampler enters the apparatus 200 via a sample line 208 from the suction force of a two way pump 212. If desired, appropriate valves 216 are opened, so that acid, dye, and/or stain can be injected into the flow to dissolve carbonates, or help enhance the particulate discrimination provided by the cameras 220.

The two way pump 212 allows for fluid 204 to be pulled from the formation using actuator valves 216, depending on the direction of the piston travel in the pump 212. Some or all of the fluid 204 that conveys particulate matter is directed to one or more camera modules 224. Motors, such as servo motors, can be used to adjust the depth and focus of the cameras 220 and the zoom. The cameras can also comprise fixed-focus units, with a depth of focus configured to include the face of a window 228 in contact with the fluid. In some embodiments, the window 228 is made from polished sapphire, including synthetic sapphire which has a very high hardness and will not scratch or divot easily. Glass, minerals (including quartz), and other optically transparent materials can also be used to fabricate the window 228.

The cameras 220 can be kept dry, or immersed in an oil-filled chamber (shown in FIG. 2A) to balance pressure. The cameras 220 may have different levels of magnification. For example, a micro camera can be used to image microfossils, and a nano camera, having a level of magnification about 1000 times greater than the micro camera, can be used to image nanofossils. Compound lenses can be used to provide both levels of magnification in a single camera 220 including one or more intermediate magnifications between the two levels. Separate cameras 220 may provide a level of redundancy, and additional image processing speed. The digital cameras themselves may also utilize digital zooming by varying the size of pixels used to process an image or view an object.

In many embodiments, the cameras 220 use a lens 234 that is configured to observe the majority of the window surface. However, in some embodiments (not shown), the cameras 220 can be offset from the center of the observation window 228, and the window 228 and compression piston 244 can be rotated with an actuator, allowing multiple images to be taken over a broader area of the observation.

A light source 232 may be used to surround the camera lens 234. High intensity light emitting diodes (LEDs) can be used to construct the source 232, as well as incandescent light, among others. If spectral imaging is utilized, the light source can be selected to interact with calcium carbonate to enhance the imaged location of fossils in the view area.

The cameras 220 may use a charged coupled device (CCD) array for taking still and video images of the fluid 204. The CCD array detects a variety of wavelengths, and filters (not shown), such as a multivariate optical element (MOE) array (similar to or identical to the MOE described in US20100245096, incorporated herein by reference in its entirety) or thin film filters, can be placed in the optical path to screen out unwanted bands of energy.

When sufficient fluid 204 has been pumped from the formation to fill the receptacle chamber, an image can be acquired. Pumps or motors 240 can be activated to move a piston 244 toward the back (i.e., the side of the window 228 facing the fluid sample) of the window 228. The piston face that engages the window 228 can be any suitable color and/or made reflective to assist in image acquisition, and fossil detection. The color and/or level of reflectivity depends on the type of dye or stain being used, if any is used at all.

The face of the piston 244 moving toward the window 228 can also be coated with a compliant material, such as rubber, that is formulated so as not to crush the particulates in the fluid 204 while holding them firmly against the window 228 to steady the particles for imaging by the camera 220. Thus, the compliance level is such that particulates in the fluid 204 are held close to the back side of the window 228, as an aid to acquiring a detailed image. Feedback can be used to adjust the level of pressure exerted on the fluid sample by the piston 244.

Turning now to FIG. 2B, it can be seen that an apparatus 200 used to implement fossil identification can take a variety of forms. In this case, the apparatus 200 can be attached to a housing, such as a collar 202 in a borehole 212. The apparatus 200 may comprise a retractable sampling probe 203 used to draw formation fluid coupled with a support pad, along with cameras, actuators, controllers, and a processor that executes instructions to acquire fluid image information, and to process fossil image information (included in the fluid image information) to recognize fossil types. A memory is included in the apparatus 200 to store a library of image data for matching operations (to identify fossil types in the fluid image information), as well as the results of recognition operations.

Thus, the apparatus 200 may include additional processors 230, memory 250, and acquisition logic 240. To aid in the image processing, parallel processing methods may also be utilized using a plurality of processor modules or multi-core processors and memory modules to accelerate the processing of still and/or moving images from the camera to identify particles, including fossils and fossil types. The apparatus 200 may also include a borehole steering control module 236, perhaps to control a rotary steerable tool located above the drill bit, to implement biosteering, as well as a telemetry module 238. Signals and data flow into and out of the apparatus 200 as needed to support image acquisition/processing operations, as well as biosteering, and transmitting information to the surface 266.

As part of a system 264 that includes one or more apparatus 200, a data processing facility 256 may be present on the surface 266. The facility 256 can be used to carry out some or all of the processing that has heretofore been described as being conducted by the apparatus 200. The facility 256 may include a telemetry receiver, processors, and memory to store instructions, models and data that can be used to implement fossil recognition activities, as well as biosteering. A display 296 can be used to display data in the form of recognition results, and biosteering decision options.

In some embodiments, data is collected from one or more camera modules, and processed by the processor(s) down hole, based on instructions that are stored in a memory, also located down hole. The operation of the camera modules is controlled by the down hole processor(s). Each camera module may have its own processor and memory to speed up image capture and processing operations including a plurality of parallel processors and memory for each camera.

The steering control module 236 may be configured to contain a model of the Earth, the drilling path, and target information. When the camera module identifies a fossil, the identification information is relayed to the down hole steering control module 236 where a processor in the steering control module 236 follows instructions on how to respond to the information by steering the bit in the borehole based on the desired location of the well relative to the fossil found, and it's position or depth below the surface. Seismic data showing undulations and dip angles/directions of various layers of interest in the Earth may constitute additional steering and target data, which may be stored at the surface, or down hole. All of the available information and data can be used to help the steering control module processor recalculate a drilling path to steer the well onto a desirable trajectory to reach the intended target.

Transmitting image information to the surface 266 may require more bandwidth than is available. The amount of information can be dramatically reduced to a few bytes (instead of millions of bytes) by using representative bit codes for identified fossil types, based on a standard library of fossil types accessed by the down hole recognition processor(s). Qualitative factor information can also be sent to the surface, perhaps representing the recognition system's probability of the image match, along with the quantity of fossils observed of each type within a given sample set.

Thus, in circumstances where high bandwidth is available (e.g., wired pipe, fiber optic, or pipe in pipe telemetry), images can be transmitted directly to the surface 266 where fossil recognition processing can be implemented. On the other hand, where bandwidth is more limited, the images acquired and calculations/identifications made by down hole processors can be stored in memory down hole, to be retrieved after the tool is pulled from the borehole 212.

Sampling commands can be initiated using surface computers (e.g., the facility 256) via downlink telemetry. Selected combinations of conditions, such as when the down hole processor senses no drilling pipe movement for at least three minutes, and no flow is detected, can also be used to initiate sampling.

The apparatus 200 may also include logic 240, perhaps comprising a programmable drive and/or sampling control system. The logic 240 can be used to acquire image data, and other data, such as acoustic noise and resistivity information.

A memory 250, located inside or outside the housing 202, can be used to store acquired data, and/or processing results (e.g., perhaps in a database). The memory 250 is communicatively coupled to the processor(s) 230. While not shown in FIG. 2, it should be noted that the memory 250 may be located down hole, or above the surface 266 of the formations.

Figure 3:
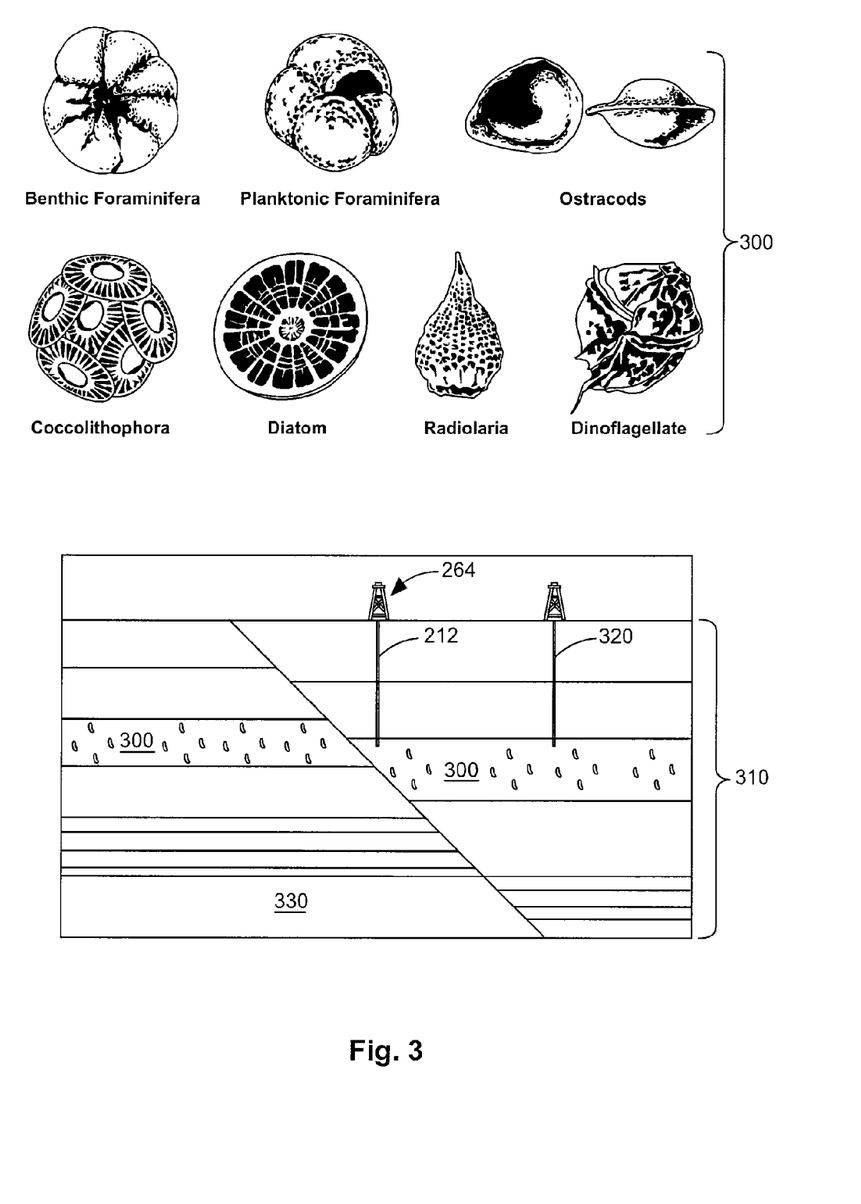
FIG. 3 illustrates fossils providing data to coordinate with offset records, according to various embodiments of the invention.

FIG. 3 illustrates fossil types 300 providing data to coordinate with offset records 310, according to various embodiments of the invention. Here the fossil types of Benthic Foraminifera, Planktonic Foraminifera, Ostracods, Coccolithophora, Diatoms, Radiolaria, and Dinoflagellates are shown. Other types can be recognized as well.

The recognition software is programmed to identify fossils, and fragments of fossils that coincide with shapes stored in a library of fossil types. Thus, internal and external shapes can be stored in a recognition library. Object recognition software available from Imagu Ltd. of Tel-Aviv, Israel, among others, can be used to recognize the fossil types. Such identification can greatly assist in determining the position of a borehole relative to the stratigraphic layers, especially when a fault is encountered.

In some embodiments, the identification of the fossil types encountered can be compared against offset records 310 from existing wells (e.g., boreholes 320) in the area, or data obtained when the current borehole 212 was itself drilled. Each set of information can be used by various embodiments of the system 264 to identify the location in the formation 330 where the image acquisition tool is currently positioned. Thus, additional embodiments may be realized.

For example, referring now to FIGS. 1-3, it can be seen that an apparatus 200 may comprise one or more fluid receptacles, a pump to move the fluid into and out of the receptacle, an imaging device (e.g., one or more cameras) to acquire fluid image information, and a processor to extract fossil image information from fluid image information, and to identify fossil types.

Thus, an apparatus 200 may comprise a fluid receptacle (e.g., the cylinder within which the piston 244 operates) having an optically transparent window 228 to contain a fluid 204 and fossils. The apparatus 200 may further comprise a pump 212 to move the fluid 204 into and out of the fluid receptacle. In most embodiments, the apparatus 200 comprises at least one imaging device (e.g., cameras 220) to acquire fluid image information from the fluid 204, where the fluid image information includes fossil image information.

The apparatus 200 may also include a processor 230 to extract the fossil image information from the fluid image information, to identify fossil types in the fluid 204 as data that associates the fossil types with a formation from which the fluid 204 was acquired, and to determine the location of a first borehole 212 in the formation based on the data and offset records associated with a second borehole 320.

Dye can be injected to enhance image contrast, and acid can be injected to dissolve the fossils. Thus, the apparatus 200 may comprise at least one of a dye injector or an acid injector 218, to inject a dye or an acid into the fluid 204 under control of the processor 230. Further, different color dyes can be rotated through a sequence of samples so the distinction of which fossil belongs to which sample set can be more easily made, should a fossil remain behind from a previous sample set.

One or more drives can be used to position the fossils against the window face. Thus, the apparatus 200 may comprise at least one reversible drive device (e.g., pumps or motors 240) to advance and retract a compliant surface (e.g., a rubber-coated surface of the piston 244) to capture the fossils against the optically transparent window 228. The window 228 in the receptacle may be made from a variety of materials, clear or colored, including synthetic sapphire, such as aluminum oxide (Al2O3) available from Rayotek Inc. of San Diego, Calif. Further embodiments may be realized.

For example, a system 264 may be constructed using one or more apparatus 200. The system 264 may comprise a down hole tool housing 202 attached to the apparatus 200. The housing 202 may comprise a wireline tool body, a MWD (measurement while drilling) down hole tool, or an LWD down hole tool.

A display can be used to view the data in real time. Thus, a system 264 may comprise a display 296 to display data comprising identified fossil types.

The system may include a transmitter, such as a telemetry transmitter, to move the data to the surface. Thus, a system 264 may comprise a transmitter as part of a telemetry module 238 to transmit at least a portion of the data to a remote processor (e.g., the facility 256).

Figure 4:
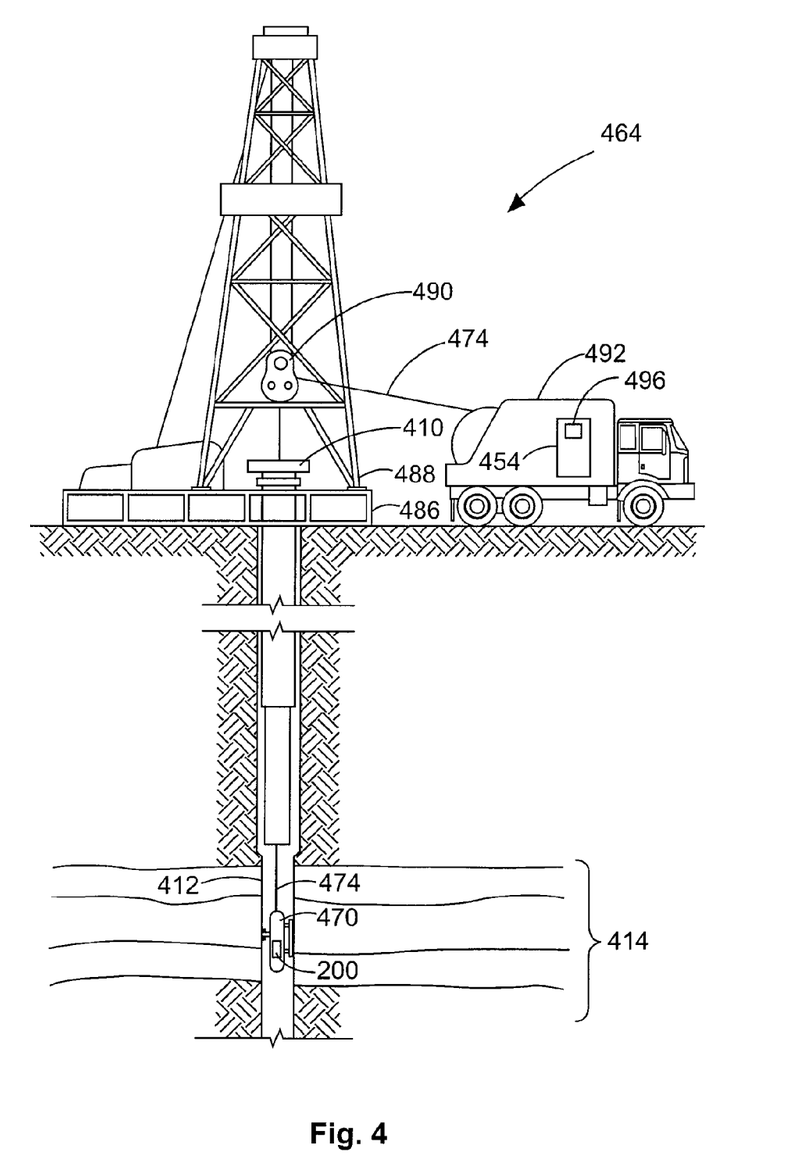
FIG. 4 illustrates a wireline system embodiment of the invention.
Figure 5:
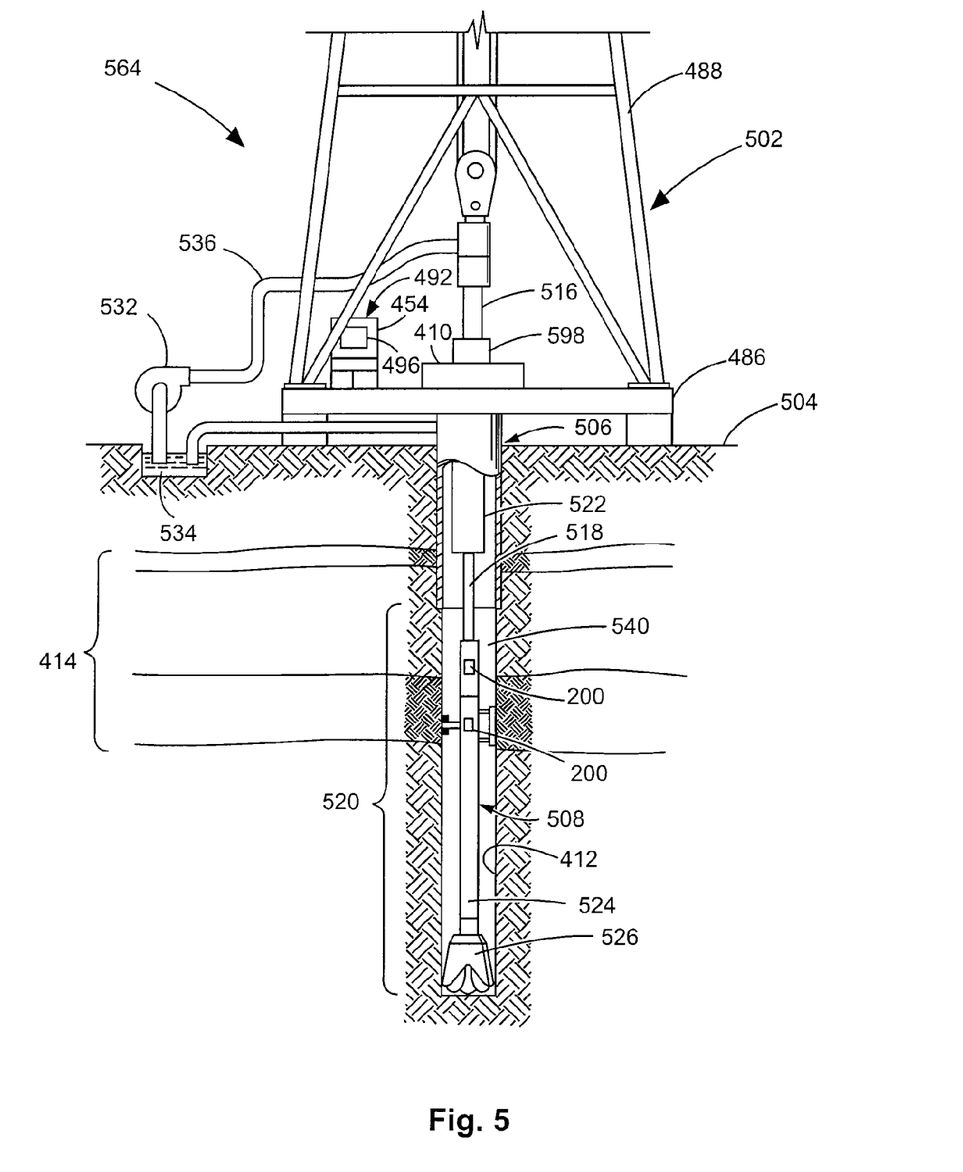
FIG. 5 illustrates a drilling rig system embodiment of the invention.

FIG. 4 illustrates a wireline system 464 embodiment of the invention, and FIG. 5 illustrates a drilling rig system 564 embodiment of the invention. Thus, the systems 464, 564 may comprise portions of a wireline logging tool body 470 as part of a wireline logging operation, or of a down hole tool 524 as part of a down hole drilling operation.

FIG. 4 shows a well during wireline logging operations. A drilling platform 486 is equipped with a derrick 488 that supports a hoist 490.

Oil and gas well drilling is commonly carried out using a string of drill pipes connected together so as to form a drilling string that is lowered through a rotary table 410 into a wellbore or borehole 412. Here it is assumed that the drilling string has been temporarily removed from the borehole 412 to allow a wireline logging tool body 470, such as a probe or sonde, to be lowered by wireline or logging cable 474 into the borehole 412. Typically, the wireline logging tool body 470 is lowered to the the region of interest and subsequently pulled upward at a substantially constant speed.

During the upward trip, at a series of depths the instruments (e.g., the apparatus 200 shown in FIGS. 2A and 2B) included in the tool body 470 may be used to perform measurements on the subsurface geological formations 414 adjacent the borehole 412 (and the tool body 470). The measurement data can be communicated to a surface logging facility 492 for storage, processing, and analysis. The logging facility 492 may be provided with electronic equipment for various types of signal processing, which may be implemented by any one or more of the components of the apparatus 200 in FIGS. 2A. and 2B Similar formation evaluation data may be gathered and analyzed during drilling operations (e.g., during LWD operations, and by extension, sampling while drilling).

For taking wireline samples, the wireline movement is temporarily halted so that a snorkle and compression pad can be extended to seal against the borehole wall. This allows fluid to be drawn from the formation. Some embodiments use expandable annular packers to seal off a depth interval, after which fluid is drawn into the sealed zone and pumped back outside of the packer-sealed area so that more formation fluid can be drawn.

In some embodiments, the tool body 470 comprises a multi-chamber sampling subsystem for obtaining and analyzing fluid samples from a subterranean formation through a wellbore. The tool is suspended in the wellbore by a wireline cable 474 that connects the tool to a surface control unit (e.g., comprising a workstation 454). The tool may be deployed in the wellbore on coiled tubing, jointed drill pipe, hard wired drill pipe, or any other suitable deployment technique.

Turning now to FIG. 5, it can be seen how a system 564 may also form a portion of a drilling rig 502 located at the surface 504 of a well 506. The drilling rig 502 may provide support for a drill string 508. The drill string 508 may operate to penetrate a rotary table 410 for drilling a borehole 412 through subsurface formations 414. The drill string 508 may include a Kelly 516, drill pipe 518, and a bottom hole assembly 520, perhaps located at the lower portion of the drill pipe 518.

The bottom hole assembly 520 may include drill collars 522, a down hole tool 524, and a drill bit 526. The drill bit 526 may operate to create a borehole 412 by penetrating the surface 504 and subsurface formations 414. The down hole tool 524 may comprise any of a number of different types of tools including MWD tools, LWD tools, and others.

During drilling operations, the drill string 508 (perhaps including the Kelly 516, the drill pipe 518, and the bottom hole assembly 520) may be rotated by the rotary table 410. In addition to, or alternatively, the bottom hole assembly 520 may also be rotated by a motor (e.g., a mud motor) that is located down hole. The drill collars 522 may be used to add weight to the drill bit 526. The drill collars 522 may also operate to stiffen the bottom hole assembly 520, allowing the bottom hole assembly 520 to transfer the added weight to the drill bit 526, and in turn, to assist the drill bit 526 in penetrating the surface 404 and subsurface formations 414.

During drilling operations, a mud pump 532 may pump drilling fluid (sometimes known by those of ordinary skill in the art as "drilling mud") from a mud pit 534 through a hose 536 into the drill pipe 518 and down to the drill bit 526. The drilling fluid can flow out from the drill bit 526 and be returned to the surface 504 through an annular area 540 between the drill pipe 518 and the sides of the borehole 412. The drilling fluid may then be returned to the mud pit 534, where such fluid is filtered. In some embodiments, the drilling fluid can be used to cool the drill bit 526, as well as to provide lubrication for the drill bit 526 during drilling operations. Additionally, the drilling fluid may be used to remove subsurface formation 414 cuttings created by operating the drill bit 526.

Thus, referring now to FIGS. 2A-2B and 4-5, it may be seen that in some embodiments, the systems 264, 464, 564 may include a drill collar 522, a down hole tool 524, and/or a wireline logging tool body 470 to house one or more apparatus 200, similar to or identical to the apparatus 200 described above and illustrated in FIGS. 2A-2B. Thus, for the purposes of this document, the term "housing" may include any one or more of a drill collar 522, a down hole tool 524, a sonde within a drill collar with access to the exterior of the collar for sample extraction, or a wireline logging tool body 470 (all having an outer wall, to enclose or attach to instrumentation, including sensors, cameras, fluid sampling devices, pressure measurement devices, transmitters, receivers, acquisition and processing logic, and data acquisition systems, among others). The tool 524 may comprise a down hole tool, such as an LWD tool or MWD tool. The wireline tool body 470 may comprise a wireline logging tool, including a probe or sonde, for example, coupled to a logging cable 474. Many embodiments may thus be realized.

For example, in some embodiments, a system 264, 464, 564 may include a display 496 to present fossil stratigraphy information, both measured and processed/calculated, as well as database information, perhaps in graphic form. A system 264, 464, 564 may also include computation logic, perhaps as part of a surface logging facility 492, or a computer workstation 454, to receive signals from transmitters and receivers, cameras, and other instrumentation to determine properties of the formation 414.

Thus, a system 264, 464, 564 may comprise a down hole tool body, such as a wireline logging tool body 470 or a down hole tool 524 (e.g., an LWD or MWD tool body), and one or more apparatus 200 attached to the tool body, the apparatus 200 to be constructed and operated as described previously.

The apparatus 200; housing 202; formation fluid 204; sample line 208; pump 212; valves 216; cameras 220; camera modules 224; window 228; processors 230; light source 232; lens 234; steering control module 236; telemetry module 238; acquisition logic 240; piston 244; memory 250; data processing facility 256; systems 264, 464, 564; display 296; rotary table 410; borehole 412; computer workstations 454; systems 464, 564; wireline logging tool body 470; logging cable 474; drilling platform 486; derrick 488; hoist 490; logging facility 492; display 496; drill string 508; Kelly 516; drill pipe 518; bottom hole assembly 520; drill collars 522; down hole tool 524; drill bit 526; mud pump 532; mud pit 534; and hose 536 may all be characterized as "modules" herein.

Such modules may include hardware circuitry, and/or a processor and/or memory circuits, software program modules and objects, and/or firmware, and combinations thereof, as desired by the architect of the apparatus 200 and systems 264, 464, 564 and as appropriate for particular implementations of various embodiments. For example, in some embodiments, such modules may be included in an apparatus and/or system operation simulation package, such as a software electrical signal simulation package, a power usage and distribution simulation package, a power/heat dissipation simulation package, and/or a combination of software and hardware used to simulate the operation of various potential embodiments.

It should also be understood that the apparatus and systems of various embodiments can be used in applications other than for logging operations, and thus, various embodiments are not to be so limited. The illustrations of apparatus 200 and systems 264, 464, 564 are intended to provide a general understanding of the structure of various embodiments, and they are not intended to serve as a complete description of all the elements and features of apparatus and systems that might make use of the structures described herein.

Applications that may include the novel apparatus and systems of various embodiments include electronic circuitry used in high-speed computers, communication and signal processing circuitry, modems, processor modules, embedded processors, data switches, and application-specific modules. Such apparatus and systems may further be included as sub-components within a variety of electronic systems, such as televisions, cellular telephones, personal computers, tablets, workstations, radios, video players, vehicles, signal processing for geothermal tools and smart transducer interface node telemetry systems, among others.

Some embodiments may operate to store down hole fluid samples so that analysis can be performed on the fluid samples at a later time, perhaps on the surface, to confirm the down hole results. These results can be confirmed by looking for fossils in the retrieved fluid samples, either down hole or on the surface. Digitized images or film images of the fossils can also be stored in the tool for later retrieval and analysis, either down hole or at the surface. Some embodiments include a number of methods.

Figure 6:
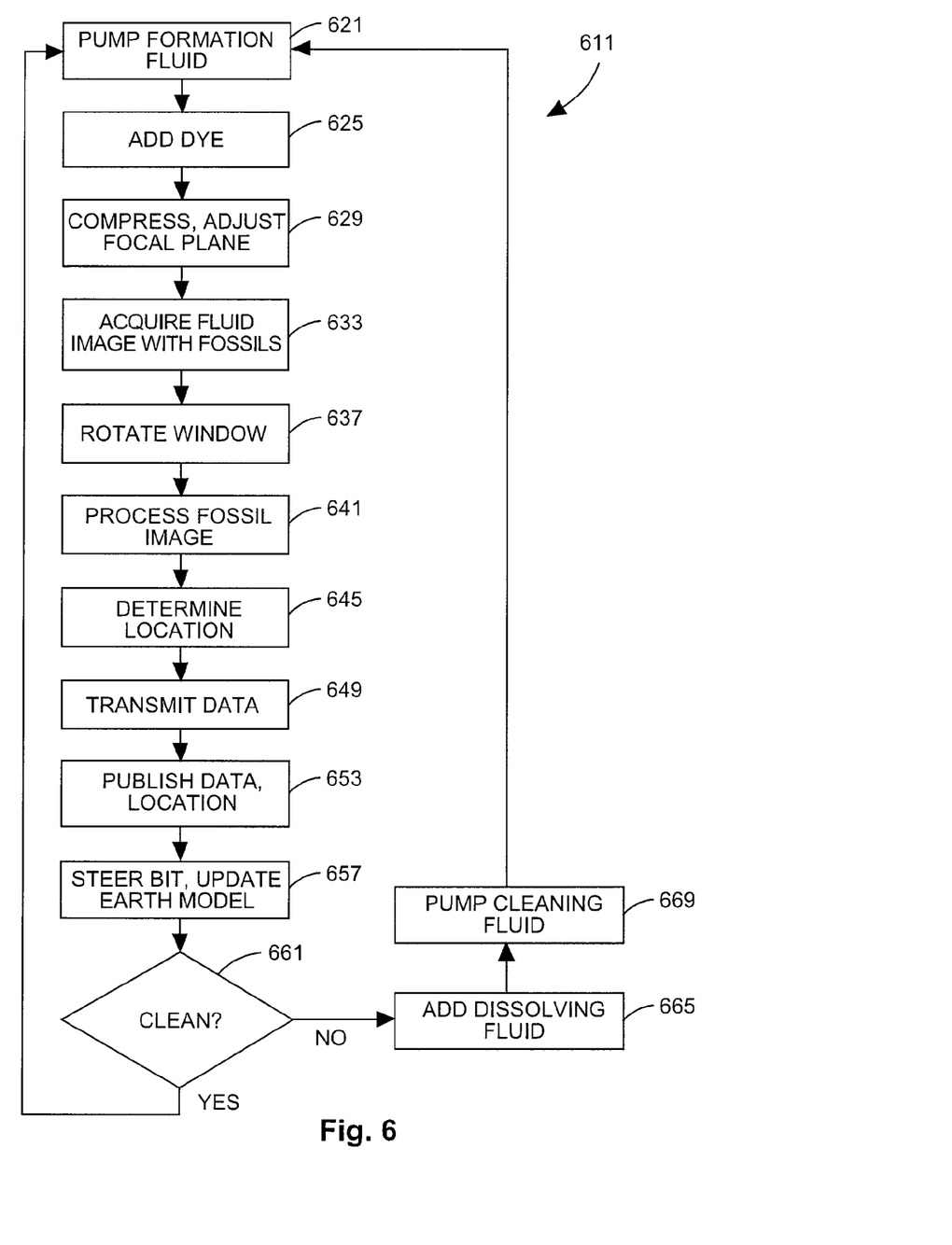
FIG. 6 is a flow chart illustrating several additional methods according to various embodiments of the invention.

For example, FIG. 6 is a flow chart illustrating several additional methods 611 according to various embodiments of the invention. The methods 611 may comprise processor-implemented methods, and may include, in more basic formats, acquiring fluid image data generated by one or more cameras, processing the data to extract fossil image information and to determine fossil types, and determining a borehole location based on the determined fossil types and offset records. The processed data can be published (e.g., stored, printed, or displayed).

Prior to image acquisition, longitudinal movement within the bore hole is halted, and the snorkel and pad are extended to seal against the bore wall. Agitation of the bore hole wall (e.g., using a brush, scraper, or other means) can be performed to encourage the release of fossils into the formation fluid if a sufficient quantity of the fossils are not already suspended in the formation fluid. The formation fluid with the suspended fossils can be moved into a windowed receptacle for viewing, and later flushed from the receptacle, perhaps by pumping water or another cleaning fluid into the receptacle. The cleaning fluid may include an acid solution to dissolve any residual fossils not flushed out of the viewing area from previous samples. The acid solution is then displaced with a new formation fluid sample.

Thus, in some embodiments, a method 611 may begin at block 621 with pumping a sample of the fluid as formation fluid into a windowed receptacle. During the activity at block 621, or prior to this activity, the formation wall may be agitated to cause fossils associated with various fossil types to mix into the fluid that is, or will be sampled. In addition, at block 621, samples of the fluid containing fossils associated with the fossil types can be stored in a container for transport. This activity can also occur later in the method 611.

Dye can be added to the fluid. Thus, the method 611 may include, at block 625, adding dye to the fluid captured between an optically transparent window and another surface (which may be opaque, or optically transparent as well, depending on the type of receptacle that is used for fluid acquisition and/or viewing).

The dye can be used for multiple purposes, including enhancing the contrast of fossils in the fluid image information, or reducing the contrast of other elements in the fluid image information (e.g., sand). Thus, the dye may be used to enhance the contrast of fossils in the fluid or to enhance the contrast of particles other than fossils in the fluid, or both.

Fossils can be captured against the window of the receptacle, using a movable, compliant surface, such as rubber. Thus, the method 611 may include, at block 629, compressing fossils in the fluid between an optically transparent window and a compliant surface. If the sample fluid is opaque, a cleaning fluid may be used to flush the area while holding the fossils against the window. Such cleaning fluids can also be used to wash the non-absorbed dye away once it has been applied to the fossils, so that the contrast of the fossils can be enhanced even further, since the dye will no longer be present in the fluid surrounding the fossils retained in the receptacle.

Focal markers can be installed proximate to the fluid to provide a reference for focusing within a three-dimensional field provided by the fluid. Therefore, the activity at block 629 may comprise adjusting the focal plane of the imaging device using focal markers on a surface used to contain the fluid. In some embodiments, the activity at block 629 includes rotating or shifting the focal plane associated with the imaging device into the field of view to focus an observation lens of the imaging device on the fossils contained in the receptacle.

The method 611 may continue on to block 633 to include acquiring fluid image information from an imaging device having a field of view including fluid, the fluid image information including fossil image information.

A window on the receptacle holding the fluid can be rotated to provide a broader search area—so that new fossils can be moved into the imaging device field of view. Thus, the method 611 may include, at block 637, rotating a windowed receptacle to move fossils into the field of view, to provide new values of the fossil image information (e.g., during the next cycle of fluid image acquisition activity).

The method 611 may continue on to block 641 to include processing the fossil image information to identify fossil types in the fluid as data that associates the fossil types with a formation from which the fluid was acquired. In some embodiments, spectral information can be used to more easily identify the location of the fossils in the fluid. Thus, the activity at block 641 may include obtaining spectral information from a fluid to augment the fluid image information and to locate fossils in the fluid.

Recognition software can be used to recognize fossil types. Thus, the activity at block 641 may include processing the fluid image information using a recognition algorithm to determine the fossil image information. For example, the algorithm may comprise a facial recognition algorithm.

As mentioned previously, offset records can be used to locate various points in a geological formation. Thus, the method 611 may continue on to block 645 to include determining the location of a first borehole in the formation based on the data and offset records associated with a second borehole.

In some embodiments, the method 611 may include, at block 649, transmitting at least a portion of the data from down hole to a surface processor. Transmission may occur via many methods, including hardwire cable (e.g., wireline cable, or MWD), wired pipe, pipe in pipe communication, wired coil tubing, and using various telemetry methods, such as mud pulse, acoustic, and electromagnetic. Thus, the activity at block 649 may include transmitting any part of the data via telemetry.

The method 611 may continue on to block 653 to include publishing the data in conjunction with indications of the location (in the formation). Trends in the fossil image data can be published; abrupt changes may indicate the presence of a fault line. Thus, the activity at block 653 may comprise publishing trends in the data.

In some embodiments, biosteering is implemented to steer a drill bit in real time, using the fossil image data. Thus, the method 611 may include, at block 657, steering a borehole drill bit based at least in part on the processed image data, including the presence or absence of selected ones of the fossil types.

Earth models can be updated in real time, using the fossil image data. Thus, the method 611 may also include, at block 657, updating an Earth formation model based on the data. The Earth model may reside in downhole memory, in surface memory or both.

The method 611 may include, at block 661, determining whether the receptacle or a window in the receptacle, are in need of cleaning. If not, then the method 611 may return to block 621.

The need for cleaning may be determined when a selected amount of transparency has been lost, for example. Or when the intensity of a reference source of illumination that shines through the window appears to have diminished by a selected degree. Fossils can be removed from the receptacle and/or window by flushing the viewing area with an acid solution to dissolve carbonates. Thus, the method 611 may continue on to block 665 to include, after processing the fossil image information, adding acid to the fluid to dissolve fossils in the fluid. The method 611 may continue on to block 669, to include pumping a cleaning fluid to flush fossils and other objects from the windowed receptacle. The method 611 may then return to block 621.

It should be noted that the methods described herein do not have to be executed in the order described, or in any particular order. For example, in some embodiments, the fluid that is initially captured in the receptacle may comprise captured fluid, and the method 611 may include adding dye and a first clean fluid to form dyed fluid that is used to flush out the captured fluid out of the fluid receptacle. The method 611 may further include washing the dyed fluid out with a second clean fluid to expose fossils associated with the fossil types between an optically transparent window and another surface forming part of the receptacle. These fossils may be more easily imaged after these activities than if they are not implemented.

Moreover, various activities described with respect to the methods identified herein can be executed in iterative, serial, or parallel fashion. The various elements of each method (e.g., the methods shown in FIGS. 1 and 6) can be substituted, one for another, within and between methods. Information, including parameters, commands, operands, and other data, can be sent and received in the form of one or more carrier waves.

Upon reading and comprehending the content of this disclosure, one of ordinary skill in the art will understand the manner in which a software program can be launched from a computer-readable medium in a computer-based system to execute the functions defined in the software program. One of ordinary skill in the art will further understand the various programming languages that may be employed to create one or more software programs designed to implement and perform the methods disclosed herein. The programs may be structured in an object-orientated format using an object-oriented language such as Java or C#. Alternatively, the programs can be structured in a procedure-orientated format using a procedural language, such as assembly or C. The software components may communicate using any of a number of mechanisms well known to those skilled in the art, such as application program interfaces or interprocess communication techniques, including remote procedure calls. The teachings of various embodiments are not limited to any particular programming language or environment. Thus, other embodiments may be realized.

Figure 7:
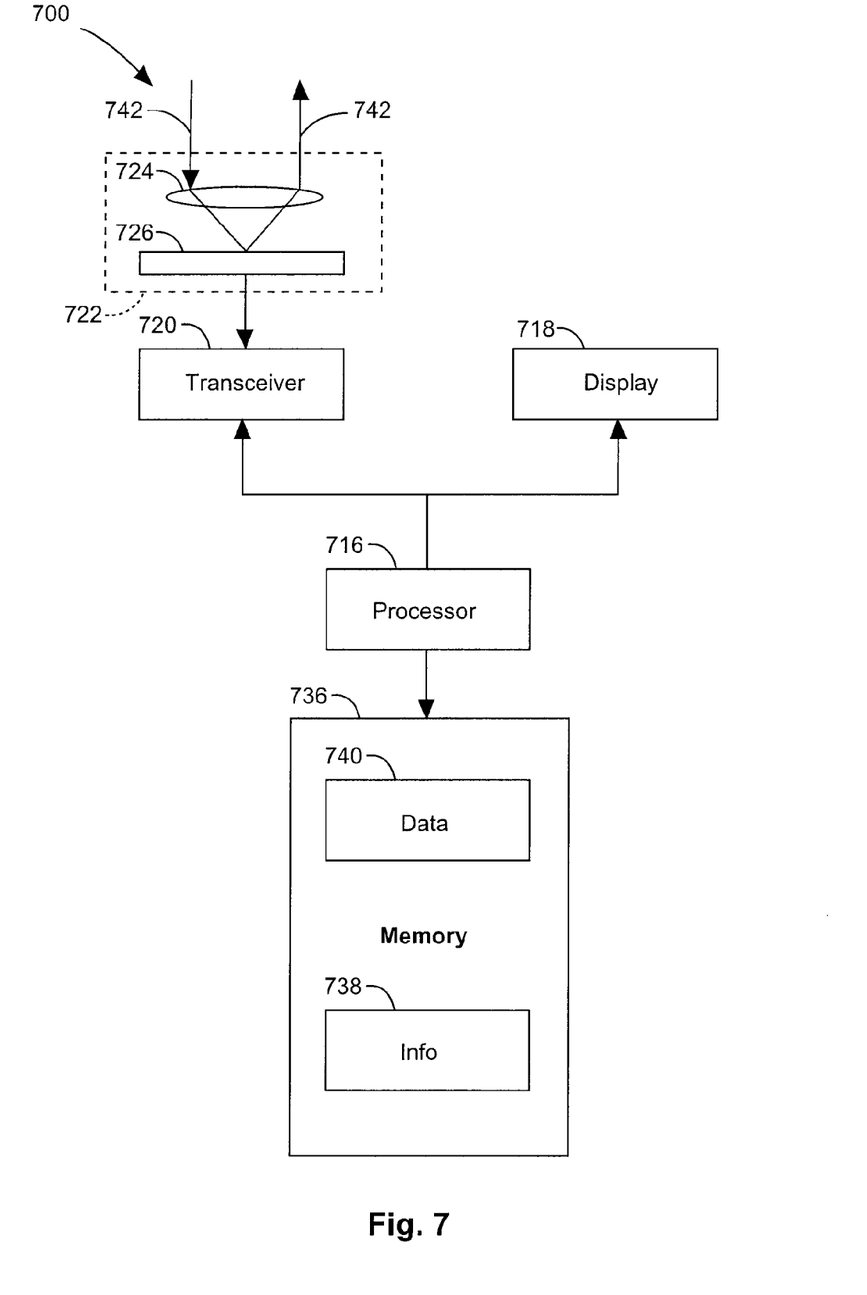
FIG. 7 is a block diagram of an article according to various embodiments of the invention.

For example, FIG. 7 is a block diagram of an article 700 of manufacture according to various embodiments, such as a computer, a memory system, a magnetic or optical disk, or some other storage device. The article 700 may include one or more processors 716 coupled to a machine-accessible medium such as a memory 736 (e.g., removable storage media, as well as any tangible, non-transitory memory including an electrical, optical, or electromagnetic conductor) having associated information 738 (e.g., computer program instructions and/or data), which when executed by one or more of the processors 716, results in a machine (e.g., the article 700) performing any actions described with respect to the methods of FIGS. 1 and 6, the apparatus of FIG. 2, and the systems of FIGS. 2, 4, and 5. The processors 716 may comprise one or more processors sold by Intel Corporation (e.g., Intel® Core™ processor family), Advanced Micro Devices (e.g., AMD Athlon™ processors), and other semiconductor manufacturers.

In some embodiments, the article 700 may comprise one or more processors 716 coupled to a display 718 to display data processed by the processor 716 and/or a wireless transceiver 720 (e.g., a down hole telemetry transceiver) to receive and transmit data processed by the processor.

The memory system(s) included in the article 700 may include memory 736 comprising volatile memory (e.g., dynamic random access memory) and/or non-volatile memory. The memory 736 may be used to store data 740 and instructions processed by the processor 716.

In various embodiments, the article 700 may comprise communication apparatus 722, which may in turn include amplifiers 726 (e.g., preamplifiers or power amplifiers) and one or more antennas 724 (e.g., transmitting antennas and/or receiving antennas). Signals 742 received or transmitted by the communication apparatus 722 may be processed according to the methods described herein.

Many variations of the article 700 are possible. For example, in various embodiments, the article 700 may comprise a down hole tool, including the tool 202 shown in FIG. 2B. In some embodiments, the article 700 is similar to or identical to the apparatus 200 shown in FIGS. 2A and 2B.

Using the apparatus, systems, and methods disclosed herein may provide the ability to discriminate between similar layers in a geological formation, to confirm the existence of a fault, and add to the stratigraphic knowledge for a particular formation. In addition, biosteering may be enabled. The combination of these advantages can significantly enhance the services provided by an operation/exploration company while at the same time controlling time-related costs.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:
1. A processor-implemented method, comprising:
acquiring digital fluid image information utilizing an imaging device in a down hole tool operated downhole in a first borehole, the imaging device having a field of view including a fluid sample, the digital fluid image information including digital fossil image information of fossils in the fluid sample, said acquiring digital fluid image information including,
drawing the fluid sample from a formation around a borehole into a sampling tool;
adding dye from a reservoir in the down hole tool to the fluid sample captured between an optically transparent window and another surface within a receptacle; and
the imaging device acquiring the digital fluid information for the captured fluid sample;
electronically comparing the digital fossil image information with one or more references to identify fossil types in the fluid sample and to generate fossil data that is representative of the identified fossil types, the fossil data associated with the formation from which the fluid sample was acquired;
determining a location of the first borehole in the formation associated with the fluid sample based on the fossil data and offset records associated with a second borehole; and publishing the fossil data in conjunction with indications of the location.

2. The method of claim 1, wherein the dye is to enhance contrast of fossils in the fluid sample or to enhance contrast of particles other than fossils in the fluid sample, or both.

3. The method of claim 1, further comprising:
after electronically comparing the digital fossil image information, adding acid from a reservoir in the down hole tool to the fluid to dissolve fossils in the fluid sample.

4. The method of claim 1, wherein the electronically comparing comprises:
electronically comparing the digital fluid image information to the one or more references using an image recognition algorithm to determine the fossil image information.

5. The method of claim 4, wherein the image recognition algorithm comprises a facial recognition algorithm.

6. The method of claim 1, further comprising:
capturing the fluid sample by pumping the fluid sample into the receptacle within the down hole tool.

7. The method of claim 6, further comprising:
pumping a cleaning fluid from a reservoir in the down hole tool to flush fossils and other objects from the windowed receptacle.

8. The method of claim 1, further comprising:
rotating the receptacle to move fossils into the field of view, to provide new values of the digital fossil image information.

9. The method of claim 1, further comprising:
obtaining spectral information from the fluid sample to augment the digital fluid image information and to locate fossils in the fluid sample.

10. The method of claim 1, further comprising:
steering a borehole drill bit during a drilling operation based at least in part on the fossil data, including presence or absence of selected ones of the fossil types.

11. The method of claim 1, further comprising:
updating an Earth formation model based on the fossil data.

12. The method of claim 1, wherein the publishing comprises:
publishing trends in the fossil data.

13. The method of claim 1, further comprising:
compressing fossils in the fluid sample between the optically transparent window and a compliant surface.

14. The method of claim 1, further comprising:
adjusting a focal plane of the imaging device using focal markers on a surface used to contain the fluid sample.

15. The method of claim 1, further comprising:
rotating or shifting a focal plane associated with the imaging device into the field of view to focus an observation lens of the imaging device.

16. The method of claim 1, further comprising:
transmitting at least a portion of the fossil data from down hole to a surface processor.

17. The method of claim 16, wherein the transmitting comprises:
transmitting the at least a portion of the fossil data via telemetry.

18. The method of claim 1, further comprising:
adding dye and a first clean fluid to form dyed fluid that is used to flush out the captured fluid from the receptacle; and
washing the dyed fluid out with a second clean fluid to expose fossils associated with the fossil types between an optically transparent window and another surface forming part of the receptacle.

19. The method of claim 1, further comprising:
agitating a wall of the formation to cause fossils associated with the fossil types to mix into the fluid.

20. The method of claim 1, further comprising:
storing the fluid sample containing fossils associated with the fossil types in a container for transport.

\* \* \* \* \*